United States Patent [19]

Fujikawa et al.

[11] Patent Number: 4,490,534

[45] Date of Patent: Dec. 25, 1984

[54] PROCESS FOR PRODUCING 3-CHLORO-5-TRIFLUOROMETHYLPYRIDINES

[75] Inventors: Kanichi Fujikawa; Yasuhiro Tsujii; Itaru Shigehara, all of Moriyama; Tatsuo Isogai, Yookaichi; Hiroshi Yoshizawa, Tokyo; Mikio Miyaji, Shiga, all of Japan

[73] Assignee: Ishihara Sangyo Kaisha Ltd., Osaka, Japan

[21] Appl. No.: 434,368

[22] Filed: Oct. 14, 1982

[30] Foreign Application Priority Data

Nov. 4, 1981 [JP] Japan ............... 56-176759

[51] Int. Cl.$^3$ ............... C07D 211/72; C07D 211/84; C07D 213/61
[52] U.S. Cl. ............... 546/345
[58] Field of Search ............... 546/345

[56] References Cited

U.S. PATENT DOCUMENTS

| | | | |
|---|---|---|---|
| 3,370,062 | 2/1968 | Corran | 546/345 |
| 4,241,213 | 12/1980 | Nishiyama et al. | 546/345 |
| 4,288,599 | 9/1981 | Nishiyama et al. | 546/345 |
| 4,331,811 | 5/1982 | Werner et al. | 546/345 |

FOREIGN PATENT DOCUMENTS

| | | | |
|---|---|---|---|
| 0013474 | 7/1980 | European Pat. Off. | 546/345 |
| 0074192 | 3/1983 | European Pat. Off. | 546/345 |
| 2477540 | 9/1981 | France | 546/345 |
| 90059 | 7/1981 | Japan | 546/345 |
| 97271 | 8/1981 | Japan | 546/345 |
| 123369 | 10/1981 | Japan | 546/345 |
| 2045245 | 8/1980 | United Kingdom | 546/345 |

Primary Examiner—Henry R. Jiles
Assistant Examiner—Robert C. Whittenbaugh
Attorney, Agent, or Firm—Oblon, Fisher, Spivak, McClelland & Maier

[57] ABSTRACT

A process for producing a 3-chloro-5-trifluoromethylpyridine derivative comprises reacting a 5-trifluoromethylpyridine derivative having a hydrogen atom at 3-position with chlorine. The process is characterized by reacting said 5-trifluoromethylpyridine derivative with chlorine in a vapor phase in the presence of a catalyst selected from the group consisting of activated carbon and a chloride of a metal element selected from the group consisting of iron, antimony, copper and zinc.

14 Claims, No Drawings

PROCESS FOR PRODUCING 3-CHLORO-5-TRIFLUOROMETHYLPYRIDINES

BACKGROUND OF THE INVENTION

1. Field of the Invention

The present invention relates to a process for producing 3-chloro-5-trifluoromethylpyridine derivatives by reacting 5-trifluoromethylpyridine derivatives with chlorine in a vapour phase in the presence of a catalyst.

2. Description of the Prior Art

Heretofore, it has been difficult to produce 5-trifluoromethylpyridine derivatives having a chlorine atom at 3-position of the pyridine ring. Particularly, it has been extremely difficult to produce the derivative having a chlorine atom at 2- and 3-positions and a trifluoromethyl group at 5-position, i.e. 2,3-dichloro-5-trifluoromethylpyridine.

Meantime, this 2,3-dichloro-5-trifluoromethylpyridine has been increasingly in demand in recent years as it is useful as an intermediate for an active ingredient for various agricultural chemicals. Therefore, it is desired to develop an industrially advantageous process for its production.

The present applicant has proposed certain processes for its production in Japanese Unexamined Patent Publications 90059/81, 97271/81 and 125369/81. However, these processes are all concerned with a liquid phase reaction. In the first two processes, 2,3-dichloro-5-trifluoromethylpyridine is produced e.g. by reacting 2-chloro-5-trifluoromethylpyridine with an aqueous ammonium solution under elevated pressure to form 2-amino-5-trifluoromethylpyridine, which is then chlorinated to form 2-amino-3-chloro-5-trifluoromethylpyridine, which is further subjected to diazotization-chlorination. These processes require a series of reaction steps, and it is necessary to conduct the reaction under elevated pressure. Besides, they involve difficulties in the treatment of the waste water. Whereas, the process disclosed in Japanese Unexamined Patent Publication 125369 is concerned with the production of 2,3-dichloro-5-trifluoromethylpyridine by reacting 2-chloro-5-trifluoromethylpyridine with chlorine in a liquid phase in the presence of a certain metal chloride as a catalyst. However, this process is economically disadvantageous in that it requires a great amount of the catalyst, for example, as much as the same amount by weight as the pyridine starting material. Further, the after-treatment of the reaction product involves difficulties, and the reaction time is rather long, for example, as long as from 15 to 20 hours.

On the other hand, it is known to chlorinate β-picoline or β-trifluoromethylpyridine in a vapour phase at an elevated temperature. However, such a process is concerned with chlorination of α-position of the pyridine ring by a radical reaction and not with chlorination of β-position. For example, U.S. Pat. No. 4,241,213 and others disclose a process for chlorination of β-picoline in a vapour phase at a temperature of from 300° to 500° C., whereby a mixture of products is obtainable which is composed mainly of those chlorinated at the side chain methyl group and α-position such as 2-chloro-5-trichloromethylpyridine and 2,6-dichloro-5-trichloromethylpyridine. U.S. Pat. No. 4,288,599 discloses a process for chlorinating and fluorinating β-picoline in a vapour phase at a temperature of from 300° to 600° C., whereby a mixture of products is obtainable which is composed mainly of those fluorinated at the side chain methyl group and chlorinated at α-position such as 2-chloro-5-trifluoromethylpyridine and 2,6-dichloro-5-trifluoromethylpyridine. Further, the publication of European Patent Application 13474 discloses a process for chlorinating β-trifluoromethylpyridine in a vapour phase at a temperature of from 300° to 450° C., whereby a mixture of products is obtainable which is composed mainly of α-chlorinated products such as 2-chloro-, 6-chloro- and 2,6-dichloro-5-trifluoromethylpyridines.

SUMMARY OF THE INVENTION

In view of the above mentioned various prior art, the present inventors initially thought that it would be extremely difficult to obtain the desired 3-chloro-5-trifluoromethylpyridine derivatives by chlorinating the corresponding 5-trifluoromethylpyridine derivatives in a vapour phase at an elevated temperature. Nevertheless, since the vapour phase chlorination is usually industrially more advantageous than the liquid phase chlorination, various studies and researches have been conducted on the vapour phase chlorination and it has been unexpectedly found that the chlorination reaction at α-position is suppressed by reacting 5-trifluoromethylpyridine with chlorine at a relatively low temperature and the chlorination proceeds preferentially or selectively at 3-position by an ionic reaction if a certain specific catalyst is present in the state where the chlorination reaction at α-position is suppressed, whereby it is possible to obtain the desired 3-chloro-5-trifluoromethylpyridine derivative.

A first object of the present invention is to provide an industrially feasible process for producing 3-chloro-5-trifluoromethylpyridine derivatives.

A second object of the present invention is to provide a process which is capable of industrially advantageously producing 3-chloro-5-trifluoromethylpyridine derivatives with use of inexpensive starting materials and by means of a simple reaction.

The present invention provides a process for producing 3-chloro-5-trifluoromethylpyridine derivatives by reacting trifluoromethylpyridine derivatives having a hydrogen atom at 3-position with chlorine, in which said pyridine derivative is reacted with chlorine in a vapour phase in the presence of at least one catalyst selected from the group consisting of activated carbon and a chloride of a metal element selected from the group consisting of iron, antimony, copper and zinc.

The other objects and features of the present invention will become apparent from the following detailed description of the preferred embodiments.

DETAILED DESCRIPTION OF THE PREFERRED EMBODIMENTS

According to the present invention, it is industrially preferred to use as the 5-trifluoromethylpyridine derivative a compound represented by the formula (I)

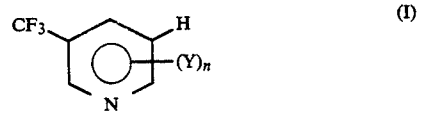

where Y is a chlorine atom or a fluorine atom and n is 0, 1 or 2, and when n is 2, Y may be the same or different, whereby a compound represented by the formula (II)

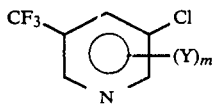

(II)

where Y is as defined above and m is 0, 1, 2 or 3, and when m is 2 or 3, Y may be the same or different, is obtainable as the desired 3-chloro-5-trifluoromethylpyridine derivative.

It is further preferred that 5-trifluoromethylpyridine or 2-chloro, 2-fluoro, 6-chloro, or 2,6-dichloro-5-trifluoromethylpyridine is used as the starting material 5-trifluoromethylpyridine derivative so as to obtain 3-chloro-5-trifluoromethylpyridine (b.p. 144°–145° C./760 mmHg), 2,3-dichloro-5-trifluoromethylpyridine (b.p. 176°–177° C./760 mmHg), 2-fluoro-3-chloro-5-trifluoromethylpyridine (b.p. 143°–144° C./760 mmHg), 3,6-dichloro-5-trifluoromethylpyridine (b.p. 182°–183° C./760 mmHg) or 2,3,6-trichloro-5-trifluoromethylpyridine (m.p. 50°–51° C.) as the 3-chloro-5-trifluoromethylpyridine derivative.

In carrying out the process of the present invention, the catalyst is packed in the reaction zone of a reactor, and the starting materials, i.e. the pyridine derivative and chlorine are supplied thereto separately or as a mixture.

The catalyst component may be composed of activated carbon alone or at least one of chlorides of metal elements selected from the group consisting of iron, antimony, copper and zinc. The chlorides of the metal elements are usually carried by a carrier such as activated carbon, zeolite or pumice. The metal chlorides include iron chloride, antimony chloride, copper chloride and zinc chloride. The metal chlorides may be directly packed in the catalyst bed. Otherwise, it is possible first to pack a compound of the above mentioned metal in the catalyst bed, and then to feed chlorine to the catalyst bed e.g. at a temperature of from 200° to 350° C. for from 1 to 5 hours to convert it into the desired chloride prior to the chlorination reaction according to the present invention. As the metal compounds, there may be mentioned oxides or hydroxides of iron, antimony, copper or zinc. The activation of the catalyst is likewise applicable to activated carbon. The carrier of the catalyst may preliminarily be formed into granules, pellets, etc. having a proper size so that the catalyst may be packed or filled in a form of either a fixed bed or fluidized bed. It is industrially preferred to use activated carbon as the carrier and to have at least one of chlorides of metals selected from the group consisting of iron, antimony, copper and zinc, carried thereon. Particularly preferred is a catalyst in which iron chloride is carried on activated carbon. The ratio of the metal chloride to the carrier is not critical, but it is usually from 2 to 40% by weight, preferably from 5 to 30% by weight, as the metal chloride, based on 1 part by weight of the carrier.

For the chlorination reaction in the process of the present invention, an inert diluent such as nitrogen, helium or argon may be used. This diluent may be introduced into the reaction tube together with other starting materials or sparately therefrom. The amount of the inert diluent is not critical but is usually within a range of from 0 to 50 moles per mole of the pyridine derivative. In the chlorination reaction of the present invention, the starting materials are usually introduced into the reaction tube in a gaseous state. For example, the pyridine derivative is vapourized and introduced into the reactor in the vapourized state. The amount of chlorine is not critical but is usually from 0.5 to 10 moles, preferably from 1 to 5 moles, per mole of the pyridine derivative. The chlorination reaction of the present invention is usually carried out at a temperature of from 150° to 400° C. When 5-trifluoromethylpyridine derivative is used as the starting material, the temperature is usually from 150° to 350° C., preferably from 180° to 320° C. When it is desired not only to substitute a chlorine atom for the hydrogen atom at β-position of the 5-trifluoromethylpyridine derivative but also the introduce a chlorine atom at any other proper position, the temperature is selected to be usually from 180° to 400° C., preferably from 200° to 350° C.

The chlorination reaction of the present invention is usually conducted under atmospheric pressure. However, it may be conducted under elevated pressure or reduced pressure, as the case requires.

In the chlorination reaction of the present invention, a product corresponding to the pyridine derivative with the hydrogen atom at 3-position substituted by a chlorine atom, is obtainable. However, in some cases, a product having chlorine atoms introduced at 3-position and at a proper additional position, is obtainable. Accordingly, according to the process of the present invention, not only the starting pyridine derivative but also the kind of the catalyst, the amount of chlorine and the reaction conditions should optionally be selected depending upon the particular type of the product desired to be thereby produced.

A gaseous mixture discharged from the reactor contains chlorinated products composed mainly of the 3-chloro-5-trifluoromethylpyridine derivatives, unreacted starting materials, hydrochloride gas as by product and in some cases an inert diluent. The mixture is passed through suitable cooling and condensing apparatus, whereupon the desired product is obtainable in a form of an oily substance, which is then purified by means of usual purifying means such as distillation or crystallization to obtain a high purity product. The recovered unreacted starting materials i.e. the pyridine derivatives are recycled to the reaction zone, whereby the yield of the desired product will be improved.

Now the present invention will be described in further detail with reference to Examples.

EXAMPLE 1

As the reactor, a vertical Inconel reaction tube having at its reaction zone a catalyst fluidized bed having an inner diameter of 30 mm and a height of 500 mm was used, and two Inconel preheating tubes having an inner diameter of 20 mm and a length of 300 mm were connected thereto. They were covered with an electric heater and heat insulator so that their temperatures could be controlled.

Into a catalyst-packing section of the reactor, 60 g of activated carbon having a particle size of from 80 to 200 mesh was introduced, and after heating the reactor to a temperature of about 200° C., chlorine gas was supplied at a rate of 1.3 l/min. for about 3 hours to activate the catalyst.

A gas mixture of 2-chloro-5-trifluoromethylpyridine and nitrogen gas was preheated to about 200° to 250° C. and fed through one of the preheating tubes to the reaction tube at such a rate that the former was 0.5 g/min. and the latter was 1.0 l/min., while a gas mixture of chlorine gas and nitrogen gas preheated to said temperature was fed through the other preheating tube to the reaction tube at such a rate that the former was 0.25 l/min. and the latter was 0.6 l/min. They were reacted at a temperature of 250° C. for about 3 hours.

The gas discharged from the reactor was condensed by passing it through a water scrubbing column and an alkaline scrubbing column. The resulting oily product was separated, washed with water and dried over sodium sulfate, whereby 77 g of an oily product was obtained. The oily product was analyzed by a gas chromatography with a temperature programmer. The results obtained are shown in the Table presented below.

EXAMPLE 2

The operation was carried out in the same manner as in Example 1 except that (i) 60 g of a catalyst obtained by mixing a solution containing 24 g of ferric chloride dissolved in 200 ml of ethanol with 120 g of activated carbon (80–200 mesh), followed by drying, was activated in the same manner as in Example 1 and (ii) the reaction was continued for 4 hours, whereby 110 g of an oily product was obtained. The results obtained by the analysis of this product are shown in the Table presented below.

EXAMPLE 3

The operation was carried out in the same manner as in Example 2 except that (i) 60 g of a catalyst comprising 12 g of copper (II) chloride carried on activated carbon was used as the catalyst and (ii) the reaction was continued for 2 hours, whereby 52 g of an oily product was obtained. The results obtained by the analysis of this product are shown in the Table presented below.

EXAMPLE 4

The operation was carried out in the same manner as in Example 2 except that (i) 60 g of a catalyst comprising 12 g of zinc chloride ($ZnCl_2$) carried on activated carbon was used as the catalyst and (ii) the reaction was continued for 2 hours, whereby 53 g of an oily product was obtained. The results obtained by the analysis of this product are shown in the Table presented below.

EXAMPLE 5

The operation was carried out in the same manner as in Example 2 except that (i) 60 g of a catalyst comprising 12 g of antimony chloride ($SbCl_3$) carried on activated carbon was used as the catalyst and (ii) the reaction was continued for 2 hours, whereby 53 g of an oily product was obtained. The results obtained by the analysis of the product are shown in the Table presented below.

EXAMPLE 6

A glass reaction tube having a diameter of 4 cm and a length of 50 cm and equipped with thermocouples was employed and the entire reaction tube was used as a catalyst packing column. Two gas supply pipes were inserted into the reaction tube through a preheater. They were covered with an electric heater and heat insulator so that their temperatures could be externally controlled. The reaction tube was placed in slant.

Into a catalyst packing section, 300 g of a catalyst obtained by mixing 250 g of granular activated carbon (particle size of from 3–8 mm) with a solution containing 50 g of anhydrous ferric chloride dissolved in 300 ml of ethanol followed by drying, was introduced. The catalyst packing column and the reaction tube were heated to a temperature of about 200° C. and chlorine gas was fed thereto at a rate of 220 ml/min. for about 3 hours to activate the catalyst.

A gas mixture of 2-chloro-5-trifluoromethylpyridine and nitrogen gas preheated to about 200° C. was fed to the reaction tube through one of the preheating tubes at such a rate that the former was 0.9 g/min. and the latter was 220 ml/min., while chlorine gas having the same temperature was fed to the reaction tube through the other preheating tube at a rate of 220 ml/min. They were reacted at a temperature of 200° C. for about 3 hours.

The gas discharged from the reactor was treated in the same manner as in Example 1, whereby 160 g of an oily product was obtained. The results obtained by the analysis of this product are shown in the Table presented below.

EXAMPLE 7

The operation was carried out in the same manner as in Example 6 except that (i) 500 g of a catalyst comprising 50 g of ferric chloride carried on zeolite (particle size of 3–4 mm) was used, and (ii) the reaction was continued for 1 hour, whereby 52 g of an oil product was obtained. The results obtained by the analysis of this product are shown in the Table presented below.

TABLE

| | Contents (%) | | | |
|---|---|---|---|---|
| | Desired products | | Unreacted materials 2-chloro-5- | |
| Example No. | 2,3-dichloro-5-trifluoromethyl-pyridine | 2,3,6-trichloro-5-trifluoromethyl-pyridine | trifluoro methyl-pyridine | Other products |
| 1 | 29.3 | 2.2 | 58.1 | 10.4 |
| 2 | 74.1 | 7.1 | 16.0 | 2.7 |
| 3 | 38.9 | 8.2 | 49.9 | 3.0 |
| 4 | 39.7 | 7.5 | 49.9 | 2.9 |
| 5 | 42.1 | 6.6 | 47.5 | 3.8 |
| 6 | 54.8 | 4.2 | 39.6 | 1.4 |
| 7 | 19.5 | 0 | 80.4 | 0.1 |

In the above Table, "Other products" are meant for products other than the desired compound, such as polychloro-5-trifluoromethylpyridine, polychloropyridine, etc.

EXAMPLE 8

The operation was carried out in the same manner as in Example 2 except that (i) 0.5 g/min. of 2-chloro-5-trifluoromethylpyridine was replaced by 0.4 g/min. of 2-fluoro-5-trifluoromethylpyridine, and (ii) the reaction was continued for 2 hours, whereby 45 g of an oily product was obtained. This product was analyzed in the same manner as in Example 2, whereby it was found that it is composed of 30% of the desired 2-fluoro-3-chloro-5-trifluoromethylpyridine, 45% of unreacted starting material 2-fluoro-5-trifluoromethylpyridine and 25% of other products.

EXAMPLE 9

The operation was carried out in the same manner as in Example 2 except that the starting material was changed to 0.6 g/min. of 2,6-dichloro-5-trifluoromethylpyridine, whereby an oily product was obtained. This product was analyzed whereby it was found that the product contained at least 70% of the desired 2,3,6-trichloro-5-trifluoromethylpyridine.

EXAMPLE 10

As the reactor, a vertical Inconel reaction tube having at its reaction zone a catalyst fluidized bed having an inner diameter of 100 mm and a height of 1,200 mm was used, and a SUS evaporator having an inner diameter of 50 mm and a length of 600 mm and two preheating tubes were connected thereto. They were covered with an electric heater and heat insulator so that their temperatures could be controlled.

Into a catalytic packing section of the reactor, 3 Kg of a catalyst comprising an anhydrous ferric chloride dissolved in water and carried on activated carbon having a particle size of from 24 to 48 mesh (20% by weight of ferric chloride was carried on the activated carbon) was introduced.

A gas mixture of 2-chloro-5-trifluoromethylpyridine and nitrogen gas was preheated to about 200° to 250° C. and fed through one of the preheating tubes to the reaction tube at such a rate that the former was 23.7 g/min. and the latter was 7.3 l/min., while a gas mixture of chlorine gas and nitrogen gas preheated to the same temperature was fed through the other preheating tube to the reaction tube at such a rate that the former was 4.4 l/min. and the latter was 7.3 l/min. They were reacted at a temperature of 280° C. for 2.5 hours.

The gas discharged from the reactor was treated in the same manner as in Example 1, whereby 3.7 kg of an oily product was obtained. The product was analyzed in the same manner, whereby it was found that the product was composed of 73.3% of the desired 2,3-dichloro-5-trifluoromethylpyridine, 10.6% of the desired 2,3,6-trichloro-5-trifluoromethylpyridine, 14.0% of unreacted starting material 2-chloro-5-trifluoromethylpyridine and 2.1% of other products.

EXAMPLE 11

The operation was carried out in the same manner as in Example 6 except that the reaction temperature was changed to 220° C., whereby 173 g of an oily product was obtained. This product was analyzed in the same manner, whereupon it was found that the product was composed of 75.0% of the desired 2,3-dichloro-5-trifluoromethylpyridine, 10.1% of the desired 2,3,6-trichloro-5-trifluoromethylpyridine, 13.9% of unreacted starting material and 1.0% of other products.

EXAMPLE 12

The operation was carried out in the same manner as in Example 6 except that (i) the reaction temperature was changed to 250° C. and (ii) the rate of chlorine gas was changed to 330 ml/min., whereby 220 g of an oily product was obtained. This product was analyzed in the same manner, whereby it was found that the product was composed of 71.0% of the desired 2,3,6-trichloro-5-trifluoromethylpyridine, 15.1% of the desired, 2,3-dichloro-5-trifluoromethylpyridine, 8.0% of unreacted starting material 2-chloro-5-trifluoromethylpyridine and 5.9% of other products.

We claim:

1. In a process for producing a 3-chloro-5-trifluoromethylpyridine derivative which comprises reacting a 5-trifluoromethylpyridine derivative having a hydrogen atom at the 3-position with chlorine, said 5-trifluoromethylpyridine derivative having the formula (I)

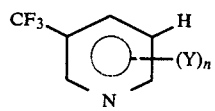

where Y is a chlorine atom or a fluorine atom and n is 0, 1 or 2, and when n is 2, Y may be the same or different, and said 3-chloro-5-trifluoromethylpyridine derivative having the formula (II)

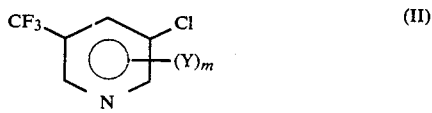

where Y is a chlorine atom or a fluorine atom and m is 0, 1, 2 or 3, and when m is 2 or 3, Y may be the same or different, the improvement which comprises reacting said 5-trifluoromethylpyridine derivative with chlorine in a vapour phase in the presence of a catalyst comprising activated carbon or activated carbon with a chloride of a metal element selected from the group consisting of iron, antimony, copper and zinc.

2. The process according to claim 1 wherein 5-trifluoromethylpyridine, 2-chloro-5-trifluoromethylpyridine, 2-fluoro-5-trifluoromethylpyridine, 6-chloro-5-trifluoromethylpyridine or 2,6-dichloro-5-trifluoromethylpyridine is used as the 5-trifluoromethylpyridine derivative to produce 3-chloro-5-trifluoromethylpyridine, 2,3-dichloro-5-trifluoromethylpyridine, 2-fluoro-3-chloro-5-trifluoromethylpyridine, 3,6-dichloro-5-trifluoromethylpyridine or 2,3,6-trichloro-5-trifluoromethylpyridine, respectively, as the 3-chloro-5-trifluoromethylpyridine derivative.

3. The process according to claim 1 wherein 2-chloro-5-trifluoromethylpyridine or 2,6-dichloro-5-trifluoromethylpyridine is used as the 5-trifluoromethylpyridine derivative to produce 2,3-dichloro-5-trifluoromethylpyridine or 2,3,6-trichloro-5-trifluoromethylpyridine, respectively, as the 3-chloro-5-trifluoromethylpyridine derivative.

4. The process according to claim 1 wherein the catalyst used is composed of a chloride of a metal element selected from the group consisting of iron, antimony, copper and zinc, which is carried on activated carbon.

5. The process according to claim 1 wherein the catalyst is composed of iron chloride carried on activated carbon.

6. The process according to claim 1 wherein the chlorination reaction is carried out at a temperature of from 150° to 400° C.

7. The process according to claim 1 wherein 2-chloro-5-trifluoromethylpyridine is chlorinated at a temperature of from 150° to 350° C. to obtain 2,3-dichloro-5-trifluoromethylpyridine.

8. The process according to claim 7 wherein the chlorination reaction is carried out at a temperature of from 180° to 320° C.

9. The process according to claim 1 wherein 2-chloro-5-trifluoromethylpyridine is chlorinated at a temperature of from 180° to 400° C. to obtain 2,3,6-trichloro-5-trifluoromethylpyridine.

10. The process according to claim 9 wherein the chlorination reaction is carried out at a temperature of from 200° to 350° C.

11. The process according to claim 1 wherein chlorine is used in an amount of from 0.5 to 10 moles per mole of the 5-trifluoromethylpyridine derivative.

12. The process according to claim 1 wherein chlorine is used in an amount of from 1 to 5 moles per mole of the 5-trifluoromethylpyridine derivative.

13. The process according to claim 1 wherein an inert diluent is used for the chlorination reaction.

14. The process according to claim 13 wherein the inert diluent is nitrogen.

* * * * *